| United States Patent [19] | [11] Patent Number: 5,068,372 |
| Kanjolia et al. | [45] Date of Patent: Nov. 26, 1991 |

[54] METHOD FOR THE SYNTHESIS OF PRIMARY ARSINES

[75] Inventors: Ravindra K. Kanjolia, North Andover; Benjamin C. Hui, Peabody, both of Mass.

[73] Assignee: CVD Incorporated, Woburn, Mass.

[21] Appl. No.: 556,787

[22] Filed: Jul. 16, 1990

[51] Int. Cl.$^5$ .................................................. C07F 9/66
[52] U.S. Cl. .......................................... 556/70; 556/64
[58] Field of Search .................................... 356/70, 64

[56] References Cited

U.S. PATENT DOCUMENTS 4,611,071  9/1986  DePriest ................................. 556/70
4,857,655  8/1989  Valentine ............................... 556/70
4,900,855  2/1990  Hui et al. ................................ 556/70

*Primary Examiner*—Arthur C. Prescott
*Attorney, Agent, or Firm*—Wayne E. Nacker; Gerald K. White

[57] ABSTRACT

Disclosed is a method for producing, from an aqueous basic composition, a primary arsine having one hydrocarbyl group bonded directly to As, the basic composition having been obtained from the combination of components comprising an alkali metal arsenite and a reactive hydrocarbyl halide by combining the aqueous composition with an acidic, nascent hydrogen-generating reducing agent to produce the primary arsine directly from the aqueous composition without isolation of the primary arsonic acid intermediate.

23 Claims, No Drawings

METHOD FOR THE SYNTHESIS OF PRIMARY ARSINES

BACKGROUND OF THE INVENTION

1. Technical Field

The present invention is directed to a new method for the preparation of primary arsines from arsonic acids, particularly to the preparation of aliphatic arsines from aliphatic arsonic acids.

2. Brief Description of Background Art

Presently, arsine gas (having a boiling point of −62.5° C.) is used in the semiconductor industry, for example, in the fabrication of gallium arsenide for use in making various high speed electronic devices and for use as a dopant in HgCdTe technology. It will be readily appreciated that the degree of purity of starting materials for use in such technological applications is highly important if not critical.

Arsine gas is highly toxic, the TLV in air of AsH3 being 0.05 parts per million (ppm). Thus it requires special precautions in handling. It would be desirable to find a less volatile and less toxic substitute of high purity for arsine gas.

The present inventors considered utilizing primary arsines containing a hydrocarbyl group, particularly an aliphatic hydrocarbyl group directly bonded to the arsenic atom, As, as substitutes for arsine gas. However, it is very difficult to make highly pure primary arsines from arsonic acids without involving multiple, highly labor intensive, purification steps involving the arsonic acid intermediates.

As discussed by A. J. Quick and R. Adams (hereinafter "Quick and Adams") in "Aliphatic Arsonic And Arsinic Acids, And Aliphatic-Aromatic Arsinic Acids", *Journal of the American Chemical Society* 44, 805–816 (1922), the lack of a satisfactory method of preparation of arsonic acids has inhibited development of compounds from arsonic acids (page 806). Of all methods available for preparing primary arsenic compounds, only the Meyer reaction, has any great importance. The Meyer reaction consists in the treatment of sodium arsenite with an alkyl halide to give an arsonic acid.

Quick and Adams disclose that in the Meyer reaction the alkyl halide probably reacts with the tautomeric forms of the sodium arsenite (Na2O3AsNa) producing compounds with the alkyl radical attached to arsenic as summarized by the following equation:

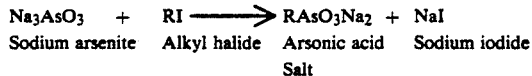

| Na3AsO3 | + | RI | ⟶ | RAsO3Na2 | + | NaI |
| Sodium arsenite | | Alkyl halide | | Arsonic acid Salt | | Sodium iodide |

At pages 806–807, Quick and Adams report that historically the procedure for making arsonic acids was tedious, and it was difficult to get rid of the "impurities" for "isolation of the product". At page 807, Quick and Adams discuss some improvements on the Meyer synthesis of arsonic acids. However, even with the improvements discussed therein, the reference teaches that for isolation of the arsonic acid it is necessary to concentrate the solution, filter off the sodium halide (an impurity) and acidify. For example, the concentration step itself is still tedious and labor intensive and accordingly not suitable for large scale production.

Page 809 describes a general procedure for making an arsonic acid from arsenious oxide, sodium hydroxide solution, an alkyl halide and hydrochloric acid (for acidification). Page 810 describes a more specific procedure for making ethyl arsonic acid, $C_2H_5As(O)(OH)_2$. As can be appreciated from the preparation of ethyl arsonic acid described therein, the procedure involves multiple concentration and filtration steps after which a quantity as specified of "needle-like crystals" separates, together with a small quantity of sodium chloride (an impurity).

The article, "Aliphatic Chloroarsines" by C. K. Banks, J. F. Morgan et al, *Journal of the American Chemical Society* 69, 927–930 (1947), generally is directed to the reaction of alkyl halides with sodium arsenite or sodium alkyl arsenites to yield alkylarsonic and dialkylarsinic acids with subsequent reduction of these products with sulfur dioxide in the presence of hydrochloric acid to yield the corresponding alkyldichloro- and dialkylchloroarsines.

The article, "Primary Arsines" by W. M. Dehn, *American Chemical Journal* 33, 101–153, (1905), at page 103 discloses a general method for preparing primary and secondary arsines. The article generally discloses that mono- and dialkyl arsenic acids of the types: $R_2AsOOH$ and $RAsO(OH)_2$ reduce by means of zinc and hydrochloric acid to secondary and primary arsines respectively. It also generally discloses that the reduction can be conducted using aromatic arsenic acids and specifically discloses that phenyl arsonic acid can be so reduced to produce monophenyl arsine.

U.S. Pat. No. 4,900,855 to Hui et al is directed to a method for providing highly pure mono- and dialkylarsines, particularly removing substantially all silicon-containing impurities therefrom, involving reaction of a monoalkylarsine or a dialkylarsine with either an alkali metal or an alkali metal hydrocarbyl thereby producing a solid alkali mono- or dialkylarsenide from which metal impurities can be removed by washing with appropriate solvent and/or drying in vacuo. The mono- or dialkylarsine may then be regenerated with a proton donor such as an acid, an alcohol or water.

SUMMARY OF THE INVENTION

The present inventors have discovered that highly pure, primary arsines can be produced in high yield directly from aqueous compositions formed from the combination of alkali metal arsenites (e.g., from treating arsenic trioxide, $As_2O_3$, with aqueous sodium hydroxide) and reactive hydrocarbyl halides without the multiple concentration and purification steps involved in prior art processes for isolating arsonic acid intermediates.

In one aspect, the present invention provides a method for producing, from an aqueous basic composition, a primary arsine having one hydrocarbyl group bonded directly to As, the basic composition having been obtained from the combination of components comprising an alkali metal arsenite and a reactive hydrocarbyl halide, preferably a hydrocarbyl bromide and/or hydrocarbyl chloride, by directly combining the aqueous composition with an acidic, nascent hydrogen-generating reducing agent to produce the primary arsine directly from the aqueous composition.

In another aspect, the present invention provides a method for producing a primary arsine having one hydrocarbyl group bonded directly to As comprising: (A) treating an aqueous basic composition of an alkali metal arsenite with a reactive hydrocarbyl bromide and/or hydrocarbyl chloride to produce an aqueous, first product containing an alkali metal hydrocarbylarsonate; (B) acidifying the aqueous first product with sufficient non-oxidizing acid to lower the pH of the aqueous first product to $\leq 3.0$ to form an aqueous arsonic acid-containing product; (C) optionally concentrating the aqueous arsonic acid-containing product by distillation; (D) optionally filtering precipitate from the aqueous arsonic acid-containing product; (E) reducing the aqueous arsonic acid-containing product directly with a nascent hydrogen-generating reducing agent thereby liberating the primary arsine having one hydrocarbyl group bonded directly to As; and (F) collecting the primary arsine in a suitable receiver.

In another aspect, the present invention provides a method for producing a primary arsine having one hydrocarbyl group bonded directly to As, from an aqueous basic composition obtained from the combination of components comprising an alkali metal arsenite, a reactive hydrocarbyl bromide and/or hydrocarbyl chloride and water, by acidifying the aqueous composition with sufficient non-oxidizing acid to lower the pH of the composition to $\leq 3.0$ to form an aqueous arsonic acid-containing product; and thereafter directly combining the aqueous arsonic acid-containing product with a nascent hydrogen-generating reducing agent to produce the primary arsine directly from the aqueous arsonic acid-containing product.

In a further aspect, the present invention provides a method of producing a primary aliphatic group-containing arsine comprising: (A) forming an aqueous first product by the treatment, in a basic aqueous medium, of an alkali metal arsenite with a reactive aliphatic group-containing halide to produce the first product; (B) acidifying the aqueous first product with a non-oxidizing acid to a pH of $\leq 3.00$ to produce a primary aliphatic arsonic acid-containing product; (C) thereafter reducing the primary aliphatic arsonic acid-containing product directly with a nascent hydrogen-generating reducing agent thereby liberating primary aliphatic arsine therefrom; and (D) collecting the primary aliphatic arsine in a suitable receiver

DETAILED DESCRIPTION OF THE INVENTION

In a first embodiment of the invention, the method involves directly combining a basic composition obtained from the combination of components comprising an alkali metal arsenite and a reactive hydrocarbyl bromide and/or hydrocarbyl chloride, with an acidic, nascent hydrogen-generating reducing agent to produce directly from the basic, aqueous composition a primary arsine having one hydrocarbyl group bonded directly to As.

Techniques for making the starting, basic composition containing alkali metal arsenite are well known. Typically, arsenic trioxide, $As_2O_3$ (also known as arsenious oxide, white arsenic and arsenous anhydride), is treated (dissolved) with an aqueous, concentrated solution of an alkali metal hydroxide such as sodium hydroxide or potassium hydroxide, preferably sodium hydroxide. For example, a 10 Normal (N) solution of sodium hydroxide can be used for this purpose. The resulting basic, aqueous composition is generally believed to contain an alkali metal arsenite. For example when sodium hydroxide is utilized as the base, the basic, aqueous composition is believed to contain trisodium arsenite, $Na_3AsO_3$ (sometimes written less empirically as $Na_2O_3AsNa$).

The basic, aqueous composition containing the alkali metal arsenite is combined with a hydrocarbyl halide such as a hydrocarbyl bromide and/or hydrocarbyl chloride which is reactive with the alkali metal arsenite. Preferably a hydrocarbyl bromide such as ethyl bromide is utilized. Hydrocarbyl iodides such as ethyl iodide are not preferred given their tendency to hydrolyze in aqueous, basic medium to the corresponding alcohols with corresponding depletion of the hydrocarbyl iodide starting material for reaction with the alkali metal arsenite. In general, the hydrocarbyl group of the hydrocarbyl halide may be alkyl, aryl or aralkyl and contain from 1 to 6 carbon atoms. Specific examples of such hydrocarbyl halides include: methyl bromide, methyl chloride, ethyl bromide, ethyl chloride, n-propyl bromide, n-propyl chloride, isopropyl bromide, isopropyl chloride, n-butyl bromide, n-butyl chloride, isobutyl bromide, isobutyl chloride, sec-butyl bromide, sec-butyl chloride, n-amyl bromide, n-amyl chloride, n-hexyl bromide, n-hexyl chloride, cyclohexyl bromide, cyclohexyl chloride, allyl bromide (i.e, $CH_2=CHCH_2Br$), allyl chloride, benzyl bromide (i.e., $C_6H_5CH_2Br$), benzyl chloride, chlorobenzene and parachlorotoluene. It is also preferred to utilize hydrocarbyl halides in which the hydrocarbyl group is aliphatic such as alkyl or allyl, preferably alkyl, more preferably an alkyl group selected from the group consisting of methyl, ethyl, n-propyl, isopropyl, n-butyl, isobutyl and sec-butyl.

The reaction of the alkali metal arsenite with the alkyl halide generally is conducted by refluxing the reaction mixture of alkali metal arsenite and alkyl halide for a period of from about 30 to about 200 hours, preferably from about 30 to about 60 hours, more preferably from about 50 to about 60 hours, the reflux temperature being determined by the boiling point of the alkyl halide or water (whichever is lower boiling).

In this first embodiment, the basic, aqueous composition, containing the product of the reaction of the alkali metal arsenite with the hydrocarbyl halide, is treated directly with a nascent hydrogen-generating reducing agent, typically an acidic nascent hydrogen-generating reducing agent, without isolating the arsonic acid intermediate. Without intending to be bound by any chemical theory, the acidic, nascent hydrogen-generating reducing agent is believed to convert the reaction product of the alkali metal arsenite and hydrocarbyl halide into one containing the corresponding arsonic acid as well as to reduce the corresponding arsonic acid to the corresponding primary arsine. The reduction reaction is carried out under an inert atmosphere, for example from an inert gas or preferably nitrogen, to prevent oxidation of the product primary arsine. The reduction reaction generally is carried out in a temperature range of from about 5° C. to about 25° C. or higher, preferably from about 10° C. to about 15° C. The temperature range is preferably chosen to minimize contamination of the primary arsine product with alcohol and water as it is liberated from the reaction mixture during reduction of the arsonic acid.

Typically the aqueous composition for reduction (i.e., containing arsonic acid) for any embodiment of the invention additionally comprises an alcohol such as methyl-, ethyl-, n-propyl, iso-propyl-, n-butyl-, isobutyl-, sec-butyl-, n-amyl-, n-hexyl-, cyclohexyl-, n-octyl-, and n-decyl alcohol. Without intending to be bound by any chemical theory, it is believed that the alcohol helps to dissolve and dilute the primary arsine product thereby helping to prevent condensation of the product into polymeric species. The alcohol should be miscible with water. It is preferred to select an alcohol so as to maximize the difference between the boiling point of the alcohol and the lower boiling point of the primary arsine product so as to reduce the amount of volatile material in the product during collection in the collecting receiver. However, where distillation and collection of the primary arsine product can be accomplished as soon as the primary arsine is formed during the reduction reaction, utilization of alcohol may be avoided and may be desirable.

The receiver for collecting the primary arsine liberated during the reduction reaction is generally maintained at a sufficiently low temperature to effect physical condensation of the primary arsine product in the receiver. By way of illustration, the reduction reaction for making ethylarsine in a method of the invention can be performed at about 10° C. at which temperature the vapor pressure of ethylarsine is 310 torr so that the ethylarsine will physically condense well in a receiving vessel pre-cooled to about −78° C.

Nascent hydrogen-generating reducing agents which may be employed in the method of the invention include: sodium borohydride in combination with hydrochloric acid, as well as zinc/mercury/hydrochloric acid reducing agent (i.e., a Zn/Hg/HCl reducing agent prepared from an amalgam of zinc dust and mercuric chloride and activated by hydrochloric acid). A zinc/mercury/hydrochloric acid reducing agent is preferred. The zinc/mercury amalgam can be prepared by generally known techniques in which mercuric chloride in aqueous medium is added to zinc dust and stirred until the zinc becomes shiny and the supernatant liquid becomes clear. Without intending to be bound by any chemical theory, the reduction of arsonic acid in any embodiment of the invention is thought to involve a reaction, which for the production of ethylarsine can be illustrated as follows:

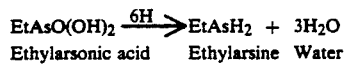

$$\text{EtAsO(OH)}_2 \xrightarrow{6H} \text{EtAsH}_2 + 3\text{H}_2\text{O}$$
Ethylarsonic acid    Ethylarsine    Water Embodiments of the method of the invention involve reduction of the respective arsonic acid intermediate directly in aqueous medium without first isolating the aforesaid intermediate, thereby greatly simplifying the preparation and rendering it more feasible on a commercial manufacturing level.

A second embodiment of the method of the invention for producing a primary arsine having one hydrocarbyl group bonded directly to As comprises the following steps. In step (A) an aqueous basic composition of an alkali metal arsenite is treated with a reactive hydrocarbyl bromide and/or hydrocarbyl chloride to produce an aqueous, first product containing an alkali metal hydrocarbylarsonate. In step (B) the aqueous first product of step (A) is acidified with sufficient non-oxidizing acid to lower the pH to ≦3.0 to form an aqueous arsonic acid-containing product. In step (C), which is optional, the aqueous arsonic acid-containing product of step (C) may be concentrated, for example by distillation. In step (D), which is optional, precipitate which may form during the acidification step (A) may be filtered out and removed from the aqueous arsonic acid-containing product. In step (E) the aqueous arsonic acid-containing product is reduced directly with a nascent hydrogen-generating reducing agent (without isolation of the respective arsonic acid intermediate) thereby liberating the primary arsine having one hydrocarbyl group bonded directly to As. As in the first embodiment described above, the aqueous composition for reduction (i.e., containing arsonic acid) additionally comprises an alcohol, examples and preferred examples of which include those which have also been described under the first embodiment of the invention. In step (F) the primary arsine liberated during the reduction step is collected in a receiver which preferably is pre-cooled.

For step (B) of this second embodiment, the acid for acidifying the product of step (A) is not particularly limited provided that it be a non-oxidizing acid. A non-oxidizing acid is employed to prevent oxidation of the product. Examples of non-oxidizing acids include: hydrochloric acid and hydrobromic acid, hydrochloric acid being preferred. The acid is gradually combined with the product of step (A) until a pH of ≦3.0, preferably between 2.0 and 3.0, is reached. At this point the aqueous composition is believed to contain the respective arsonic acid. A pH lower than 2.0 is not necessary and may result in undesirable dissolution of unreacted arsenic oxide to form arsine gas. Also, too low a pH may tend to promote generation of nascent hydrogen in the subsequent reduction step too quickly which may result in undesirable foaming of the composition.

Suitable alkali metal arsenites for step (A) of this second embodiment include those described previously herein for the first embodiment of the method of the invention, namely those formed by treatment of arsenic trioxide with aqueous, concentrated alkali metal hydroxide such as sodium hydroxide or potassium hydroxide, preferably sodium hydroxide. Suitable reactive hydrocarbyl bromides and/or hydrocarbyl chlorides for step (A) include those previously described herein for the first embodiment of the invention. Without intending to be bound by any chemical theory, the product of step (A) is believed to contain an alkali metal hydrocarbylrsenate. Nascent hydrogen-generating reducing agents for step (E) of this second embodiment include those described previously herein for the first embodiment of the invention, a zinc/mercury/hydrochloric acid reducing agent being preferred. Moreover, as for the first embodiment, collection of the primary arsine liberated during the reduction step of this second embodiment is collected in a receiving vessel (a receiver) which preferably is pre-cooled.

In a third, preferred embodiment of the method of the invention, an aliphatic group-containing halide is utilized as hydrocarbyl halide for reaction in basic aqueous medium with an alkali metal arsenite. Aliphatic group-containing halides have been described previously herein in the discussion of the first embodiment of the invention. Preferably the aliphatic group is an alkyl group selected from the group consisting of methyl, ethyl, n-propyl, isopropyl, n-butyl, isobutyl and sec-butyl, the ethyl group being particularly preferred.

In step (A) of the third embodiment, an aqueous first product is formed by the treatment, in a basic aqueous medium, of an alkali metal arsenite, preferably trisodium arsenite, with a reactive aliphatic group-containing halide, preferably wherein the aliphatic group of the aliphatic group-containing halide is a $C_1$-$C_6$ hydrocarbyl group, more preferably a hydrocarbyl group selected from the group consisting of alkyl, cycloalkyl, alkenyl and cycloalkenyl, most preferably an alkyl group selected from methyl, ethyl, n-propyl, isopropyl, n-butyl, isobutyl or sec-butyl. In step (B) the aqueous first product of step (A) is acidified with a non-oxidizing acid to a pH of $\leq 3.00$, preferably to between 2.0 and 3.0, to produce a primary aliphatic arsonic acid-containing product. Suitable and preferred non-oxidizing acids include those described previously herein under the second embodiment. Thereafter, in step (C), the primary aliphatic arsonic acid-containing product of step (B) is directly reduced (i.e., without isolation of the respective primary aliphatic arsonic acid intermediate of step B) with a nascent hydrogen-generating reducing agent thereby liberating primary aliphatic arsine therefrom. Suitable and preferred nascent hydrogen-generating reducing agents include those described previously herein under the first embodiment of the invention. As in the first embodiment described above, the aqueous composition for reduction (i.e., containing arsonic acid) additionally comprises an alcohol, examples and preferred examples of which include those which have also been described under the first embodiment of the invention. In step (D) the liberated primary aliphatic arsine is collected in a suitable receiver.

Where desired, residual water and/or alcohol may be removed from the primary arsine product produced by any embodiment of the method of the invention by distillation using generally known distillation techniques.

Primary arsine products produced by methods of the invention have utility, for example, as a replacement for arsine gas used in the semiconductor industry, for example, in the fabrication of gallium arsenide for making various high speed electronic devices and as a dopant in HgCdTe technology.

The following example is provided to illustrate more specifically the method of the invention and should not be construed as a limitation thereof.

EXAMPLE 1

This example illustrates the preparation of ethylarsine, $EtAsH_2$, according to a method of the invention.

(a) Preparation of ethyl arsonic acid.

A 12 liter (l) three neck flask was equipped with a water circulated condenser, addition funnel and mechanical stirrer. Next, 1192 grams (g; 6 moles) of arsenic trioxide, $As_2O_3$, was dissolved in 10 normal (N) NaOH solution (3.6 l) and transferred into the 3 neck flask. Then, 1630 g (15 moles) of ethyl bromide, $C_2H_5Br$, was added dropwise to the solution. The contents of the flask were refluxed continuously for 55 hours at 43° C. pot temperature. Thereafter, the contents of the flask were cooled to room temperature and 12 N hydrochloric acid was added to the contents of the flask until a pH of 3 was observed via pH paper and congo red. The solution became turbid and some precipitate formed. Some volatiles and some water (total volume of 2 l) were distilled off. Some more precipitate formed upon standing. The solution was filtered via a filter funnel and distilled water was added to make a total volume of 6 l. Thus a 2 molar solution of ethyl arsonic acid, $EtAsO(OH)_2$, was obtained.

(b) Preparation of Zn/Hq amalgam.

A glass apparatus was set up with a 22 l 3-neck flask, condenser, mechanical stirrer and addition funnel. 36 moles (2.34 kilograms) of Zn dust was added to this and 2.0 l of deionized $H_2O$ was added to the resulting composition. 1.65 moles (450 g) of mercuric chloride, $HgCl_2$, was added to this and washed with 500 milliliters (ml) of $H_2O$. 1.5 l of ethanol was added and the suspension was degassed by evacuating and backfilling with $N_2$ gas. The contents were stirred overnight in a nitrogen, $N_2$, atmosphere.*

* Alternatively the following preparation of Zn/Hg amalgam could be utilized. A glass apparatus is set up with a 22 l 3-neck flask, condenser, mechanical stirrer and addition funnel. 36 moles (2.34 kilograms) of Zn dust is added to this and 2.0 l of deionized $H_2O$ is added to the resulting composition. Next, 1.0 l of 0.5 M nitric acid is added. After 30 minutes of stirring the solutions are decanted and zinc dust is washed twice with deionized water and 2.0 l of deionized water is added to the resulting composition. Next, 1.65 moles of mercuric chloride is added and the resulting suspension is stirred overnight. On the next day the supernatant liquid is decanted and a mixture of 2 l of deionized water with 1.5 l of ethanol is added. The contents of the flask are degassed by evacuating and backfilling with nitrogen gas.

(c) Reduction of ethyl arsonic acid of part (a).

On the next day, 6 moles of $EtAsO(OH)_2$ of part (a) above (previously degassed) was added to the reactor and HCl acid was added slowly. The rate of $H_2$ generation was monitored via a mineral oil bubbler. As the reaction progressed, $EtAsH_2$ was condensed in the receiver. Scrubbers containing concentrated $HNO_3$ (alternatively 5% bleach solution could be used) were attached to the exit end of the bubbler. The addition of 7 of 12 N HCl was completed over a period of two working days (16 hours) and a total of 450 g $EtAsH_2$ was collected. This corresponded to an overall yield of 71%. Ethylarsine was purified by distillation.

What is claimed is:

1. A method for producing, from an aqueous basic composition, a primary arsine having one hydrocarbyl group bonded directly to As, said basic composition obtained from the combination of components comprising an alkali metal arsenite and a reactive hydrocarbyl bromide and/or hydrocarbyl chloride, by directly combining said aqueous composition with a nascent hydrogen-generating reducing agent to produce said primary arsine directly from said aqueous composition.

2. The method of claim 1 wherein the hydrocarbyl group of said hydrocarbyl bromide and/or said hydrocarbyl chloride is selected from the group consisting of alkyl, aryl and aralkyl.

3. The method of claim 1 wherein the hydrocarbyl group of said hydrocarbyl bromide and/or said hydrocarbyl chloride is an alkyl group selected from the group consisting of methyl, ethyl, n-propyl, isopropyl, n-butyl, isobutyl and sec-butyl.

4. The method of claim 1 wherein said alkali metal arsenite comprises trisodium arsenite.

5. The method of claim 1 wherein said nascent hydrogen-generating reducing agent comprises a zinc/mercury amalgam in hydrochloric acid.

6. A method for producing a primary arsine having one hydrocarbyl group bonded directly to As comprising:

(A) treating an aqueous basic composition of an alkali metal arsenite with a reactive hydrocarbyl bromide and/or hydrocarbyl chloride to produce an aqueous, first product containing an alkali metal hydrocarbylarsonate;

(B) acidifying said aqueous first product with sufficient non-oxidizing acid to lower the pH to $\leq 3.0$ to form an aqueous arsonic acid-containing product;

(C) thereafter, optionally concentrating said aqueous arsonic acid-containing product by distillation;

(D) thereafter, optionally filtering precipitate from said aqueous arsonic acid-containing product;

(E) reducing said aqueous arsonic acid-containing product directly with a nascent hydrogen-generating reducing agent thereby liberating said primary arsine having one hydrocarbyl group bonded directly to As; and (F) collecting said primary arsine in a receiver.

7. The method of claim 6 wherein the hydrocarbyl group of said hydrocarbyl bromide and/or said hydrocarbyl chloride is selected from the group consisting of alkyl, aryl and aralkyl.

8. The method of claim 6 wherein the hydrocarbyl group of said hydrocarbyl bromide and/or said hydrocarbyl chloride is an alkyl group selected from the group consisting of methyl, ethyl, n-propyl, isopropyl, n-butyl, isobutyl and sec-butyl.

9. The method of claim 6 wherein said alkali metal arsenite comprises trisodium arsenite.

10. The method of claim 6 wherein said non-oxidizing acid is hydrochloric acid.

11. The method of claim 6 wherein said nascent hydrogen-generating reducing agent comprises a zinc/mercury amalgam in hydrochloric acid.

12. A method for producing a primary arsine having one hydrocarbyl group bonded directly to As, from an aqueous basic composition obtained from the combination of components comprising an alkali metal arsenite, a reactive hydrocarbyl bromide and/or hydrocarbyl chloride and water, by acidifying said aqueous composition with sufficient non-oxidizing acid to lower the pH to $\leq 3.0$ to form an aqueous arsonic acid-containing product; and thereafter directly combining said aqueous arsonic acid-containing product with a nascent hydrogen-generating reducing agent to produce said primary arsine directly from said aqueous arsonic acid-containing product.

13. The method of claim 12 wherein the hydrocarbyl group of said hydrocarbyl bromide and/or said hydrocarbyl chloride is selected from the group consisting of alkyl, aryl and aralkyl.

14. The method of claim 12 wherein the hydrocarbyl group of said hydrocarbyl bromide and/or said hydrocarbyl chloride is an alkyl group selected from the group consisting of methyl, ethyl, n-propyl, isopropyl, n-butyl, isobutyl and sec-butyl.

15. The method of claim 12 wherein said alkali metal arsenite comprises trisodium arsenite.

16. The method of claim 12 wherein said non-oxidizing acid is hydrochloric acid.

17. The method of claim 12 wherein said nascent hydrogen-generating reducing agent comprises a zinc/mercury amalgam in hydrochloric acid.

18. A method of producing a primary aliphatic group-containing arsine comprising:

(A) forming an aqueous first product by the treatment, in a basic aqueous medium, of an alkali metal arsenite with a reactive aliphatic group-containing halide to produce said product;

(B) acidifying said aqueous first product with a non-oxidizing acid to a pH of $\leq 3.00$ to produce a primary aliphatic arsonic acid-containing product;

(C) thereafter reducing said primary aliphatic arsonic acid-containing product directly with a nascent hydrogen-generating reducing agent thereby liberating primary aliphatic arsine therefrom; and (D) collecting said primary aliphatic arsine in a receiver.

19. The method of claim 18 wherein the aliphatic group of said aliphatic group-containing halide is a $C_1$–$C_6$ hydrocarbyl group.

20. The method of claim 18 wherein the $C_1$–$C_6$ hydrocarbyl group is selected from the group consisting of alkyl, cycloalkyl, alkenyl and cycloalkenyl.

21. The method of claim 18 wherein the $C_1$–$C_6$ hydrocarbyl group is an alkyl group selected from methyl, ethyl, n-propyl, isopropyl, n-butyl, isobutyl or sec-butyl.

22. The method of claim 18 wherein said alkali metal arsenite comprises trisodium arsenite.

23. The method of claim 18 wherein said non-oxidizing acid is hydrochloric acid.

* * * * *